US010485648B2

(12) United States Patent
Choi et al.

(10) Patent No.: US 10,485,648 B2
(45) Date of Patent: Nov. 26, 2019

(54) MOBILE BIO-SCAFFOLD CONTROLLED BY MAGNETIC FIELD AND METHOD OF MANUFACTURING THE SAME

(71) Applicant: Daegu Gyeongbuk Institute of Science and Technology, Daegu (KR)

(72) Inventors: Hong Soo Choi, Daegu (KR); Sang Won Kim, Daegu (KR); Seung Min Lee, Gyeongsangbuk-do (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 666 days.

(21) Appl. No.: 14/735,967

(22) Filed: Jun. 10, 2015

(65) Prior Publication Data

US 2015/0351897 A1    Dec. 10, 2015

(30) Foreign Application Priority Data

Jun. 10, 2014   (KR) .................. 10-2014-0070349

(51) Int. Cl.
*A61F 2/02* (2006.01)
*A61L 27/38* (2006.01)
(Continued)

(52) U.S. Cl.
CPC .............. *A61F 2/022* (2013.01); *A61L 27/04* (2013.01); *A61L 27/50* (2013.01); *A61L 27/54* (2013.01); *A61L 27/58* (2013.01); *A61F 2210/0004* (2013.01); *A61F 2210/009* (2013.01); *A61F 2240/00* (2013.01); *A61L 2300/64* (2013.01)

(58) Field of Classification Search
CPC ............... A61F 2/022; A61F 2210/009; A61B 1/00158; A61B 34/30; A61L 27/04; A61L 27/50; A61L 27/54; A61L 27/58
See application file for complete search history.

(56) References Cited

U.S. PATENT DOCUMENTS 5,911,731 A * 6/1999 Pham ............... A61B 17/12022
140/92.1

FOREIGN PATENT DOCUMENTS

KR    10-1441739 B1    9/2014
KR    10-1458938 B1    11/2014

OTHER PUBLICATIONS

Sangwon Kim et al., "Fabrication and Characterization of Magnetic Microrobots for Three-Dimensional Cell Culture and Targeted Transportation", Advanced Materials (www.MaterialsViews.com), vol. 2013, No. 25, p. 5863-5868, 2013 Published by WILEY-VCH Verlag GmbH & Co. KGaA, Weinheim.

(Continued)

*Primary Examiner* — Nathan R Price
*Assistant Examiner* — Justin L Zamory
(74) *Attorney, Agent, or Firm* — Masuvalley & Partners (57) ABSTRACT

A mobile bio-scaffold controlled by a magnetic field is provided. A mobile bio-scaffold controlled by a magnetic field according to the present invention comprises a spherical body including a first ring, a second ring connected to the first ring that intersects the second ring, and a third ring connected to the first and second rings that intersect the third ring, with a plurality of openings being defined by the first to third rings. A magnetic layer is disposed on the spherical body. The spherical body rotates through interaction between the magnetic layer and a rotational magnetic field applied from an external source, thereby moving by rolling in a single direction.

6 Claims, 4 Drawing Sheets

(51) Int. Cl.
*A61L 27/50* (2006.01)
*A61L 27/54* (2006.01)
*A61L 27/04* (2006.01)
*A61L 27/58* (2006.01)

(56) References Cited

OTHER PUBLICATIONS

Soukeyna Bouchebout et al., "An overview of multiple DoF magnetic actuated micro-robots", HAL archives-ouvertes.fr, HAL Id:hal-00767603 (https://hal.archives-ouvertes.fr/hal-00767603), Dec. 20, 2012, p. 1-19.

* cited by examiner

MOBILE BIO-SCAFFOLD CONTROLLED BY MAGNETIC FIELD AND METHOD OF MANUFACTURING THE SAME

CROSS REFERENCE TO RELATED APPLICATION

The present application claims priority from Korean Patent Application Number 10-2014-0070349 filed on Jun. 10, 2014, the entire contents of which are incorporated herein for all purposes by this reference.

BACKGROUND OF THE INVENTION

Field of the Invention

The present invention relates to a mobile bio-scaffold controlled by a magnetic field and a method of manufacturing the same. More particularly, the present invention relates to a mobile bio-scaffold controlled by a magnetic field and a method of manufacturing the same, in which the bio-scaffold has a magnetic layer such that the bio-scaffold can be controlled by a magnetic field applied from an external source.

Description of Related Art

Recently, biomedical engineering, in particular, tissue engineering pertaining to the treatment and regeneration of tissue is developing.

Tissue engineering is a field of applied science that investigates the correlation between the structure and the function of biological tissue by applying the basic concepts and technologies of life science and engineering in an integrative manner. Tissue engineering is intended to maintain, improve, or restore the functions of human bodies by producing a substitute of the biological tissue and implant the substitute in a living body.

However, although high-level medical engineering technologies have grown dramatically, internal organs and tissue of human bodies are frequently injured, and organ transplant surgeries for treating such injuries still have a variety of problems, such as technical difficulties, high costs, the lack of donors, and side effects caused by the use of immunosupressants.

As a new approach to the organ transplant, necessity for the development of artificial internal organs or the regeneration of tissue using tissue engineering is significantly increasing.

The basic principle of tissue engineering includes sampling necessary tissue from a body of a patient, isolating a cell from the tissue, cultivating the isolated cell on a scaffold, thereby manufacturing a cell-scaffold complex, and implanting the cell-scaffold complex in the body of the patient.

The cell-scaffold complex must satisfy not only in vivo stability, but also a variety of conditions. First, the scaffold must be formed of a material that is beneficial to the enhancement of the attachment, propagation, and differentiation of a cell. The scaffold must have an overall porous structure able to promote the propagation of a cell and the regeneration of tissue. Superior interconnection between the pores of the porous structure is required.

In addition, the bio-scaffold must be biocompatible, and the pores are required in order to provide a wide surface area such that an implanting cell can be easily integrated to tissue. The bio-scaffold must be formed of a biodegradable material according to the positions to which the bio-scaffold is applied.

Bio-scaffolds currently in use are generally used for the regeneration of, for example, bones, skins, and internal organs. The shape of the scaffold structure and the size of the pores are determined according to cells and tissues to be transplanted on bio-scaffolds. These are very important factors since the formation of new tissue on the scaffold structure is significantly influenced by the porosity, size, and three-dimensional (3D) interconnected pore structure of the scaffold structure. A suitable porous structure is necessary in order to carry a sufficient number of cells, and the interconnected pore structure is necessary for the diffusion of nutritional elements.

Recently, research and development are continuously being carried out for the manufacture of bio-scaffolds that can be effectively and reliably used for the treatment and regeneration of tissues.

For example, Korean Patent Application Publication No. 10-2013-0120572 (published on Nov. 5, 2013) disclosed "POROUS THREE-DIMENSIONAL STRUCTURE CONTAINING CELLS AND METHOD OF MANUFACTURING THE SAME."

However, in the related art, such a bio-scaffold must be directly inserted into a living body and be fixed to an intended position by a surgical method or an assistance of a machine in order to insert the bio-scaffold into a living body and position the bio-scaffold on an implant site. However, this method involves the risk of infection and injury during the insertion of the scaffold. In addition, this method is restrictively applicable to a localized portion, access to which is difficult, or a blood vessel or brain tissue, the exposure of which externally from the human body may be fatal.

The information disclosed in the Background of the Invention section is only provided for better understanding of the background of the invention and should not be taken as an acknowledgment or any form of suggestion that this information forms prior art that would already be known to a person skilled in the art.

RELATED ART DOCUMENT

Patent Document 1: Korean Patent Application Publication No. 10-2013-0120572 (published on Nov. 5, 2013)

BRIEF SUMMARY OF THE INVENTION

Various aspects of the present invention provide a mobile bio-scaffold controlled by a magnetic field that has superior biocompatibility and can precisely and rapidly move to a target point in response to a magnetic field applied from an external source.

Also provided is a mobile bio-scaffold controlled by a magnetic field that is spherical in order to improve a propulsion efficiency when the bio-scaffold moves by rolling in response to a magnetic field applied from an external source.

In an aspect of the present invention, a mobile bio-scaffold includes: a spherical body including a first ring, a second ring connected to the first ring that intersects the second ring, and a third ring connected to the first and second rings that intersect the third ring, with a plurality of openings being defined by the first to third rings; and a magnetic layer disposed on the spherical body. The spherical body rotates through interaction between the magnetic layer and a rotational magnetic field applied from an external source, thereby moving by rolling in a single direction.

According to an embodiment of the present invention, the spherical body may be formed of a resin material or a biodegradable material that biologically decomposes within a human body.

The magnetic layer may cover a portion or an entire area of the spherical body.

The spherical body may further include a protective layer formed of a biocompatible material.

The spherical body having the plurality of openings carries may have cells cultivated in an internal space thereof.

In another aspect of the present invention, provided is a method of manufacturing a mobile bio-scaffold. The method includes: forming a spherical body including a first ring, a second ring connected to the first ring that intersects the second ring, and a third ring connected to the first and second rings that intersect the third ring, with a plurality of openings being defined by the first to third rings; and forming a magnetic layer on an outer surface of the spherical body, the magnetic layer allowing the spherical body to interact with a rotational magnetic field applied from an external source.

According to an embodiment of the present invention, the method may further include, after the step of forming the magnetic layer, forming a protective layer of a biocompatible material covering the magnetic layer.

The method may further include, after the step of forming the magnetic layer, cultivating cells within the spherical body having the plurality of openings.

According to the present invention as set forth above, the following effects may be realized:

(1) It is possible to prevent side effects during the process of insertion into the human body due to the superior biocompatibility of the bio-scaffold.

(2) It is possible to directly carry cells to a localized portion of the human body, a blood vessel, or brain tissue without surgical intervention or the assistance of a machine by controlling the movement of the bio-scaffold using a rotational magnetic field applied from an external source.

The methods and apparatuses of the present invention have other features and advantages that will be apparent from, or are set forth in greater detail in the accompanying drawings, which are incorporated herein, and in the following Detailed Description of the Invention, which together serve to explain certain principles of the present invention.

DETAILED DESCRIPTION OF THE INVENTION

Reference will now be made in detail to various embodiments of the present invention in conjunction with the accompanying drawings so that a person skilled in the art to which the present invention relates could easily put the present invention into practice. In the following detailed description of the structural principle of exemplary embodiments of the present invention, detailed descriptions of known functions and components incorporated herein will be omitted in the case that the subject matter of the present invention is rendered unclear.

Reference should be made to the drawings, in which the same reference numerals and symbols will be used throughout the different drawings to designate the same or like components.

In addition, throughout this document, when an element is referred to as being "connected to" or "coupled to" another element, not only it can be "directly connected" or "coupled to" the other element, but also it can be "indirectly connected or coupled to" the other element via an "intervening" element. Furthermore, it will be understood that the terms "comprise," "include," "have," and any variations thereof used herein are intended to cover a non-exclusive inclusion unless explicitly described to the contrary.

Figure 1:
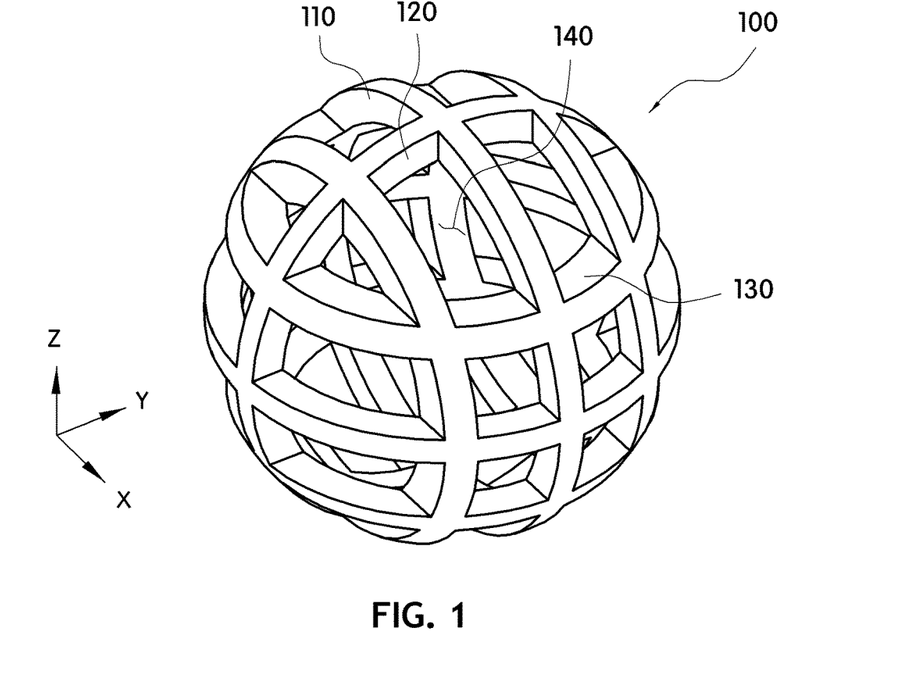
FIG. 1 is a perspective view illustrating the overall configuration of a mobile bio-scaffold controlled by a magnetic field according to an exemplary embodiment of the present invention.

Throughout this document, X, Y, and Z axes refer to three axes that perpendicularly intersect each other, in which the X axis indicates a direction parallel to an imaginary plane defined by a first ring with respect to FIG. 1, the Y axis indicates a direction normal to the imaginary plane, and Z axis indicates a direction parallel to the imaginary plane and normal to the X axis and Y axis.

The technical features of a mobile bio-scaffold controlled by a magnetic field and a method of manufacturing the same according to exemplary embodiments of the present invention make it possible to control the movement of the bio-scaffold using a rotational magnetic field applied from an external source, whereby cells can be carried to a localized portion of the human body, such as tissue within the human body or a microvasculature.

A mobile bio-scaffold controlled by a magnetic field 10 according to an exemplary embodiment of the present invention includes a spherical body 100 and a magnetic layer 200.

FIG. 1 is a perspective view illustrating the overall configuration of a mobile bio-scaffold controlled by a magnetic field according to an exemplary embodiment of the present invention.

Referring to FIG. 1, the spherical body 100 defines therein a space where cells 20 can be cultivated. The spherical body 100 is substantially in a spherical shape formed by intersecting and connecting first rings 110, a second ring 120, and third rings 130 to each other in order to increase the efficiency of transporting the cells 20.

Figure 2:
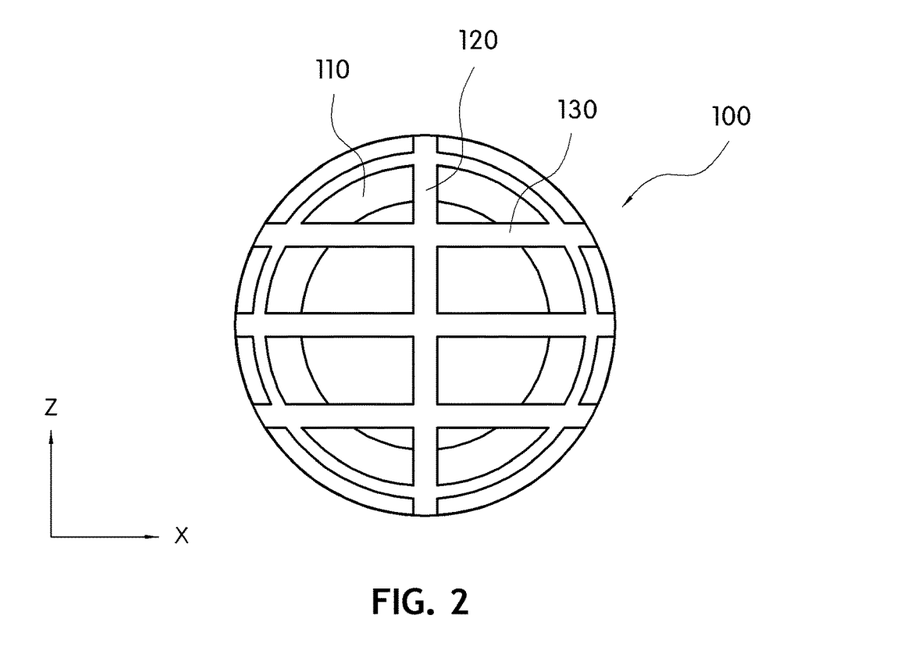
FIG. 2 is an end view illustrating the XZ plane of the mobile bio-scaffold controlled by a magnetic field according to the exemplary embodiment of the present invention.
Figure 3:
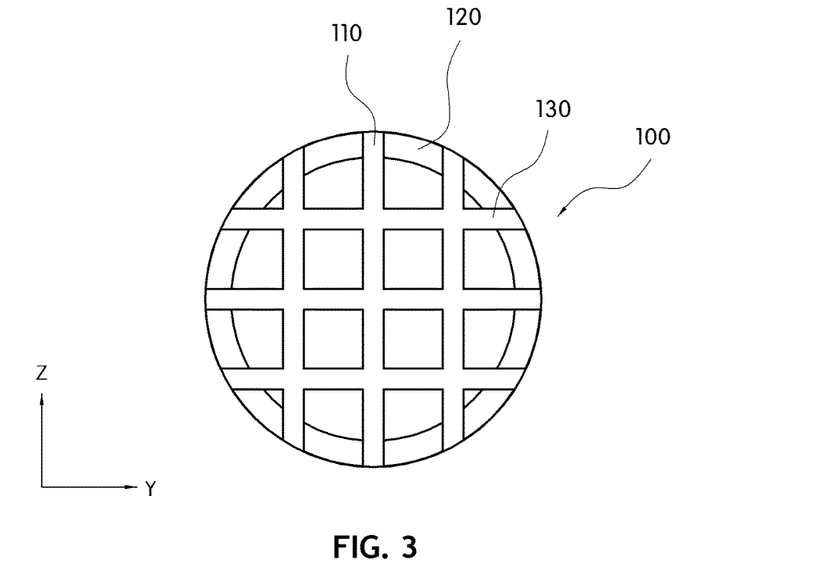
FIG. 3 is an end view illustrating the YZ plane of the mobile bio-scaffold controlled by a magnetic field according to the exemplary embodiment of the present invention.

FIG. 2 and FIG. 3 are end views illustrating the XZ and YZ planes of the mobile bio-scaffold controlled by a magnetic field according to the present exemplary embodiment.

Referring to FIG. 2, the first rings 110 are positioned on the XZ plane such that the first rings 110 have a circular end surface, and the second ring 120 is connected to the firsts ring 110 that perpendicularly intersect the second ring 120. In addition, the third rings 130 are oriented horizontally with respect to the paper surface, and are connected to the first ring 110s and the second ring 120 that intersect the third rings 130.

Referring to FIG. 3, the second ring 120 is positioned on the YZ plane such that the second ring 120 has a circular end surface, and the first rings 110 are connected to the second ring 120 that perpendicularly intersects the first rings 110. In addition, the third rings 130 are oriented horizontally with respect to the paper surface, and are connected to the first rings 110 and the second ring 120 that intersect the third rings 130.

With this configuration, the mobile bio-scaffold controlled by a magnetic field 10 can be formed such that one cross-section cut by the XY-, YZ, and XZ planes is circular on the XYZ coordinates.

Although the first to third rings have been circular rings, this is not intended to be limiting. The first to third rings may be elliptical rings or may be in other shapes in which circular rings and elliptical rings are combined.

Figure 4:
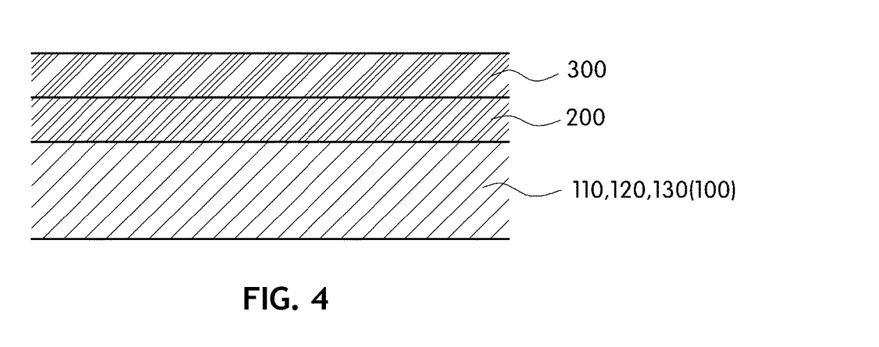
FIG. 4 is an enlarged cross-sectional view illustrating the mobile bio-scaffold controlled by a magnetic field according to the exemplary embodiment of the present invention.

FIG. 4 is an enlarged cross-sectional view illustrating the mobile bio-scaffold controlled by a magnetic field according to the exemplary embodiment of the present invention.

Referring to FIG. 4, a magnetic layer 200 and a protective layer 300 may be provided on the outer surface of the spherical body 100 including the first to third rings.

The spherical body 100 may be formed of any material and in any shape as long as the material and the shape can be used for a typical bio-scaffold. The spherical body 100 may be formed of a resin material, such as polymer, ceramics, or nanofiber. The spherical body 100 may be formed of a biodegradable material, bio-degradable, a bio-adhesive, a bio-inert material, or a biodegradable magnetic material that can biologically decompose within a human body.

The spherical body 100 having a microscopic size may be formed from a photocurable polymer by lithography. Due to having a microscopic size, the spherical body 100 can easily move within a living body.

The photocurable polymer refers to a type of polymer that cures when irradiated with light. The photocurable polymer may be selected from among any types of polymers without being specifically restricted as long as the polymers can form a three-dimensional (3D) bio-scaffold by lithography. It is preferable that the photocurable polymer be one selected from among, but not limited to, SU-8 polymer, KMPR, IP-L, and IP-G, or mixtures thereof. It is more preferable that the photocurable polymer be SU-8 polymer.

The magnetic layer 200 disposed on the outer surface of the spherical body 100 makes it possible to control the movement of the bio-scaffold 10 using a magnetic field applied from an external source. It is therefore possible to position the bio-scaffold 10 on an implant site without surgical intervention or the assistance of a machine.

The magnetic layer 200 may be formed of a metal, which has a certain level of magnetism, and the degree of corrosiveness (reactivity) of which is insignificant. It is preferable that the metal composition of the magnetic layer 200 be one selected from among nickel (Ni), iron (Fe), cobalt (Co), and neodymium (Nd), or mixtures thereof. It is more preferable that the metal composition contain Ni.

Accordingly, the spherical body 100 can rotate through interaction between the magnetic layer 200 and a rotational magnetic field applied from an external source, thereby moving by rolling in a single direction. In this manner, the spherical body 100 can carry the cells 20 to a target point of the human body.

Although the magnetic layer 200 has been illustrated and described as being disposed on the entire outer surface of the spherical body 100, this is not intended to be limiting. The magnetic layer 200 may be selectively formed on the inner surface, the outer surface, the first rings 110, the second ring 120, or the third rings 130 of the spherical body 100. Alternatively the magnetic layer 200 may be formed on portions of the outer surface of the spherical body 100, for example, on intersecting points or portions of the rings.

Figure 5:
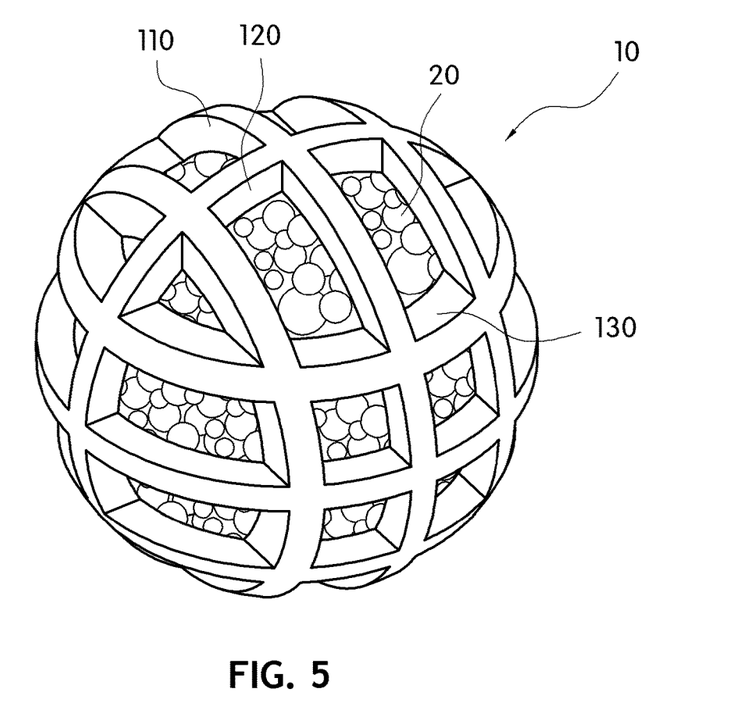
FIG. 5 is a perspective view illustrating the state of using the mobile bio-scaffold controlled by a magnetic field according to the exemplary embodiment of the present invention in which cells are cultivated.

FIG. 5 is a perspective view illustrating the state of using the mobile bio-scaffold controlled by a magnetic field according to the exemplary embodiment of the present invention in which cells are cultured.

As illustrated in FIG. 5, the spherical body 100 has a plurality of openings 140 defined by the first to third rings 110 to 130 that are connected to and intersect each other, since the first rings 110 are spaced apart predetermined distances from each other and the third rings 130 are spaced apart predetermined distances from each other. The special-purpose cells 20 to be used for the regeneration of skins or bones are cultivated within then inner space of the spherical body 100 through the openings 140, thereby converting the bio-scaffold 10 to a cell-scaffold complex.

However, this is not intended to be limiting, and a medicine may be contained in the internal space of the spherical body 100, such that the bio-scaffold 10 can carry the medicine to a target point of the human body.

The sizes of the openings 140 may be adjusted by connecting the first to third rings 110 to 130 to each other according to cells and tissues to be transplanted on the bio-scaffold 10. However, the sizes of the openings 140 are not specifically restricted.

Figure 6:
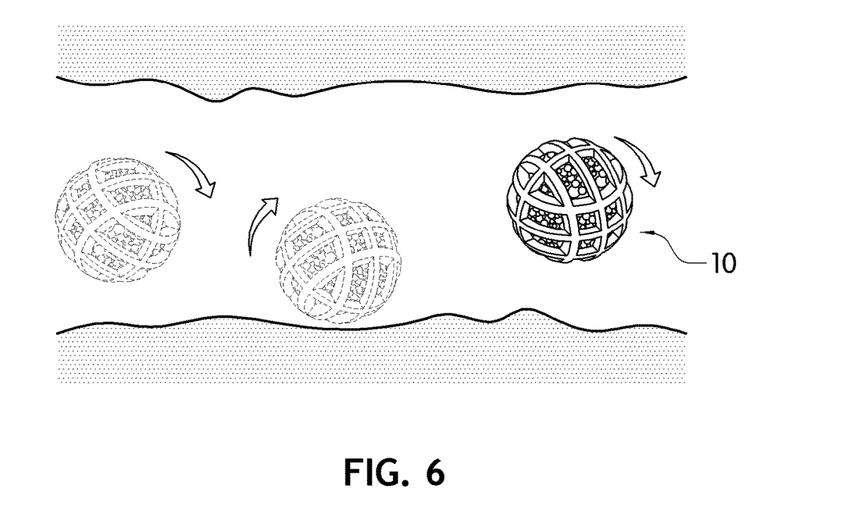
FIG. 6 illustrates the operating state of the mobile bio-scaffold controlled by a magnetic field according to the exemplary embodiment of the present invention.

FIG. 6 illustrates the operating state of the mobile bio-scaffold controlled by a magnetic field according to the exemplary embodiment of the present invention.

As illustrated in FIG. 6, the bio-scaffold 10 is in the shape of a cell-scaffold complex produced by cultivating the cells 20 to be implanted within the openings 140 or the inner space of the bio-scaffold 10. The bio-scaffold 10 is implanted into a human body using a device such as an endoscope (not shown). The bio-scaffold 10 is required to cause no side-effects.

For this, as illustrated in FIG. 4, the spherical body 100 has a protective layer 300 covering the entire outer surface in order to prevent side-effects within a living body. However, this is not intended to be limiting, and the protective layer 300 may be formed to cover the entire outer surface of the magnetic layer 200.

It is preferable that the protective layer 300 be formed of a material having superior biocompatibility. The material may be one selected from among titanium (Ti), medical grade stainless steel, alumina ($Al_2O_3$), and gold (Au), or mixtures thereof. It is preferable that the material contain Ti.

Reference will now be made to a method of manufacturing the mobile bio-scaffold controlled by a magnetic field as configured above.

Figure 7:
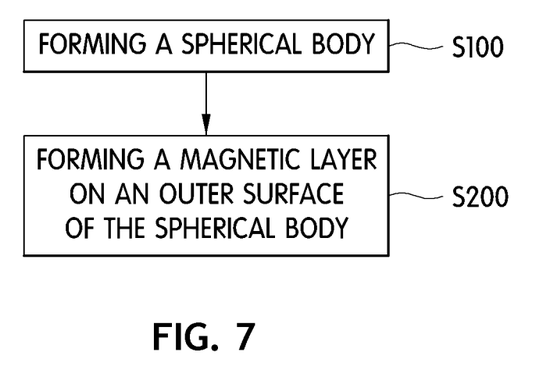
FIG. 7 is a flowchart illustrating a method of manufacturing a mobile bio-scaffold controlled by a magnetic field according to the exemplary embodiment of the present invention.

The method of manufacturing the mobile bio-scaffold controlled by a magnetic field according to an exemplary embodiment of the present invention includes: a step of forming a spherical body (S100); and a step of forming a magnetic layer on the outer surface of the spherical body (S200).

At the step of forming the spherical body forms the spherical body 100 (S100), the cells 20 could be carried while serving as a main body in which the cells 200 are cultivated. The spherical body 100 includes the first rings 110, the second ring 120 connected to the first rings 110 that intersect the second ring 120, and the third rings 130 connected to the first and second rings 110 and 120 that that intersect the third rings 130, with the plurality of openings 140 being defined by the first to third rings 110 to 130.

The spherical body may be formed by a typical method of manufacturing a bio-scaffold, which is one selected from among, but is not limited to, particulate leaching, emulsion freeze-drying, high pressure gas expansion, phase separation, fused deposition modeling (FDM), and lithography.

It is preferable that the bio-scaffold controlled by a magnetic field having a 3D structure be manufactured from a photocurable polymer by lithography.

At the step of forming the magnetic layer (S200), the magnetic layer 200 is formed on the outer surface of the spherical body 100. The magnetic layer 200 allows to control the movement of the spherical body 100 through the interaction between the spherical body 100 and a rotational magnetic field applied from an external source.

The magnetic layer may be formed by a typical coating method without being specifically restricted. It is preferable that the coating method be one selected from among, but not limited to, electron beam deposition, dipping, electroplating, sputtering, and chemical vapor deposition.

Accordingly, the mobile bio-scaffold controlled by a magnetic field according to the present embodiment can carry the cells 20 to a target point of the human body, such as a localized portion thereof, a blood vessel, or brain tissue, the exposure of which externally from the human body may be fatal, without surgical intervention or the assistance of a machine unlike in the related art.

After the step of forming the magnetic layer, the outer surface of the magnetic layer 200 may be coated with a biocompatible metal in order to improve in vivo stability and bio-compatibility.

The biocompatible metal may be selected from among any metals without being specifically restricted as long as the metals are stable in vivo and have superior biocompatibility. It is preferable that the biocompatible metal be one selected from among titanium (Ti), medical grade stainless steel, alumina ($Al_2O_3$), and gold (Au), or mixtures thereof. It is preferable that the biocompatible metal contain Ti The biocompatible metal may be formed by a typical coating method without being specifically restricted like the magnetic material. It is preferable that the coating method be one selected from among, but not limited to, electron beam deposition, dipping, electroplating, sputtering, and chemical vapor deposition.

After the step of forming the magnetic layer, the cells to be carried to the target point may be cultivated or a medicine may be contained in the plurality of openings and the internal space of the spherical body.

As set forth above, the mobile bio-scaffold controlled by a magnetic field and the method of manufacturing the same according to the present invention can prevent side effects during the process of insertion into the human body and during use therein due to the superior biocompatibility of the bio-scaffold. It is possible to directly carry cells to a localized portion of the human body, a blood vessel, or brain tissue without surgical intervention or the assistance of a machine by controlling the movement of the bio-scaffold using a rotational magnetic field applied from an external source.

It should be understood that the present invention is not limited by the embodiments as set forth above and the drawings as attached. A person skilled in the art will appreciate that various substitutes, modifications, and changes are possible without departing from the scope and spirit of the present invention.

What is claimed is:

1. A mobile bio-scaffold comprising:
a spherical body comprising a plurality of first rings having a plurality of first central axes, a second ring having a second central axis and connected to the first rings that intersects the second ring at points where the first rings and the second ring intersect, and a plurality of third rings having a plurality of third central axes and connected to the first and second rings that intersect the third rings,
wherein each of the first to third rings forms an intersecting complete loop,
wherein said plurality of the first rings are parallel to each other and intersect perpendicularly to the second ring and said plurality of the third rings, wherein said plurality of the third rings are parallel to each other and intersect perpendicularly to the first rings and the second ring, wherein the second ring intersects perpendicularly the first and third rings, and
wherein a plurality of openings being formed among the first to third rings, wherein when a magnetic layer is disposed on the spherical body, the spherical body formed by asymmetric positioning of the first rings, the second ring and the third rings forms a plurality of asymmetric magnetic axes with respect to each ring, wherein a combination of each of a magnetic axis forms a combined magnetic axis at a center of the spherical body orientated across a three-dimensional coordinate space of the spherical body based on the locations of said plurality of first rings, said second ring and said plurality of third rings; and
and
wherein the spherical body rotates by interaction between a rotational magnetic field applied from an external source and the magnetic axis, thereby moving by rolling in a single direction.

2. The mobile bio-scaffold according to claim 1, wherein the spherical body comprises one or more selected from the group consisting of a resin material, a biodegradable material, a biodegradable magnetic material, a biocompatible material, a bio-adhesive, and a bio-inert material, the bio-degradable material, the biodegradable magnetic material, the biocompatible material, the bio-adhesive, and the bio-inert material being able to biologically decompose within a human body.

3. The mobile bio-scaffold according to claim 1, wherein the magnetic layer covers a portion or an entire area of the spherical body.

4. The mobile bio-scaffold according to claim 1, wherein the spherical body further comprises a protective layer formed of one or more selected from a biocompatible material, a bio-degradable, a bio-adhesive, and a bio-inert material.

5. The mobile bio-scaffold according to claim 1, wherein the spherical body having the plurality of openings carries cells cultivated in an internal space thereof and contains a medicine therein.

6. A mobile bio-scaffold comprising:
a spherical body comprising a plurality of first rings, a second ring that is connected to the first rings that intersect the second ring at points where the first rings and the second ring cross each other, and a plurality of third rings that are connected and intersected to the first rings and the second ring, wherein each of the first to third rings forms an intersecting complete loop, wherein said plurality of the first rings are parallel to each other and intersect perpendicularly to the second ring and said plurality of the third rings, wherein said plurality of the third rings are parallel to each other and intersect perpendicularly to the first rings and the second ring, wherein the second ring intersects perpendicularly the first and third rings, wherein a plurality of openings being formed among the first to third rings, and wherein when a magnetic layer is disposed on the spherical body, the spherical body formed by asymmetric positioning of the first rings, the second ring and the third rings forms a plurality of asymmetric magnetic axes with respect to each ring, wherein a combination of each of a magnetic axis forms a combined magnetic axis at a center of the spherical body orientated across a three-dimensional coordinate space of the spherical body based on the locations of said plurality of first rings, said second ring and said plurality of third rings; and wherein the spherical body rotates by interaction between a rotational magnetic field applied from an external source and the magnetic axis, thereby moving by rolling in a single direction.

\* \* \* \* \*